United States Patent [19]

Niswender

[11] 4,336,185

[45] Jun. 22, 1982

[54] FOLIC ACID DERIVATIVES

[75] Inventor: Gordon D. Niswender, Fort Collins, Colo.

[73] Assignee: Rohm and Haas Company, Philadelphia, Pa.

[21] Appl. No.: 69,144

[22] Filed: Aug. 23, 1979

Related U.S. Application Data

[60] Continuation of Ser. No. 868,368, Jan. 10, 1978, abandoned, which is a division of Ser. No. 663,037, Mar. 2, 1976, abandoned.

[51] Int. Cl.$^3$ ............................................ C07D 475/04
[52] U.S. Cl. ............................. 260/112 R; 23/230 B; 260/112.5 R; 424/1; 544/261
[58] Field of Search .................... 544/261; 260/112 R, 260/112.5 R

[56] References Cited

U.S. PATENT DOCUMENTS

| | | | |
|---|---|---|---|
| 3,855,208 | 12/1974 | Rutner et al. | 424/1 |
| 3,925,355 | 12/1975 | Piasio et al. | 424/1 |
| 3,988,431 | 10/1976 | Giuas et al. | 23/230 B |
| 3,989,812 | 11/1976 | Barrett et al. | 23/230 B |
| 4,028,465 | 6/1977 | Lewin et al. | 23/230 B |

OTHER PUBLICATIONS

Balakrishman, *Chemical Abstracts*, vol. 80, (1974), 130087.

*Primary Examiner*—Paul M. Coughlan, Jr.
*Attorney, Agent, or Firm*—Terence P. Strobaugh

[57] ABSTRACT

Novel protein conjugates and radioiodinated derivatives of folic acid and salts, esters and amides useful in the radioimmunoassay (RIA) of body fluids to determine folic acid are disclosed.

1 Claim, No Drawings

FOLIC ACID DERIVATIVES

This is a continuation of application Ser. No. 868,368 filed Jan. 10, 1978 which is a division of application Ser. No. 663,037 filed Mar. 2, 1976 both now abandoned.

This invention relates to novel protein conjugates and iodinated conjugates of folic acid and its salts, esters and amides which retain the ability to competitively bind on a binding protein, such as folic acid binding globulin or on an antibody which is specific to folic acid. The new compounds are useful in analysis of body fluids such as blood serum, blood plasma, urine and the like, to assay for the presence of folic acid by competitive protein binding assay (CPSA) or by radioimmunoassay (RIA) procedures.

The conjugates of folic acid of this invention have the following structural formula:

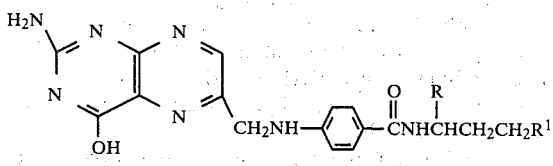 I wherein R and $R^1$ are carboxy or a radical of the formula

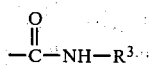

wherein $NHR^3$ is a protein radical derived from thyroglobulin, methylated bovine serum albumin (BSA), sheep serum albumin (SSA), rabbit gamma globulin (RGG), porcine serum albumin (PSA), human serum albumin (HSA) and the like or a radical of the formula:

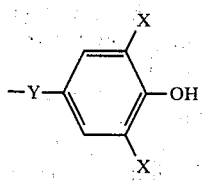 A wherein Y is:
(a)

wherein $R^4$ is alkyl, for example, alkyl having from 1 to 18 carbon atoms and preferably having from 1 to 2 carbon atoms, such as methyl, ethyl, isopropyl, n-butyl, lauryl, stearyl and the like or (b) alkylene, for example, alkylene having from 1 to 18 carbon atoms and preferably alkylene having from 1 to 3 carbon atoms such as methyl, ethyl, propyl, octyl, octadecyl and the like and X is hydrogen, $^{125}I$ or $^{131}I$ with the proviso that one of the R and $R^1$ substituents is carboxy or a salt, ester or amide thereof.

Those compounds having the radical "A" substituent wherein both X's are hydrogen are readily iodinatable to introduce radioactive iodine in either or both of the X positions. The resulting radioactive derivatives can competitively bind with folic acid on a binding protein, such as folic acid binding globulin or an antibody generated in the blood stream of a vertebrate by an antigenic protein conjugate of folic acid. The products of the present invention are therefore quite useful in the determination of folic acid by competitive protein binding assay (CPBA) or by radioimmunoassay (RIA).

Since it is not possible to iodinate folic acid, it has not been possible to use a gamma counter in RIA for folic acid. These novel compounds which can be iodinated and behave as an iodinated folic acid now permit the use of gamma counters rather than employing a liquid scintillation counter. Use of radioiodine also results in higher specific activity labelled compounds thereby greatly improving the sensitivity of the assay.

The conjugates of folic acid (I. supra) are prepared by the use of a water-soluble carbodiimide condensing agent. In making these compounds wherein $R^3$ is a protein, folic acid is converted to its mono-salt, such as the monosodium or other alkali metal mono-salt by reaction with an alkali metal carbonate or bicarbonate. The resulting folic acid salt is separated by precipitation with an organic solvent, for example, acetone and the like, filtered, washed and dried. The protein is dissolved in water and a carbodiimide salt, such as the hydrochloride, the methyl-p-toluene sulfonate, the hydroacetate, the sulfate, or the like, is added and then the folic acid salt is added. The several reactants may be mixed in any order in the aqueous medium. The relative proportion between them may be varied depending upon the extent of substitution desired. For example, the number of moles of folic acid salt used in the reaction may range from about two to one hundred or more per mole of protein. The reaction may be carried out at a temperature in the range of from room temperature to about 50° C., but preferably at room temperature, the time employed being from several hours at the lower temperature to five minutes at the higher temperature. After the reaction, the conjugate is separated in any suitable fashion. For example, it may be purified by removing unreacted components from the reacted mixture by dialysis against running water for a number of hours and then against a suitable buffer at a pH of 7.5. The product may be dried as by lyophilization.

Similarly, those compounds wherein $R^3$ is radical A may be produced by mixing a folic acid salt with a carbodiimide salt and with a salt of the amine, such as the hydrochloride or of the ester of the amino acid such as tyrosine methyl ester. In general, the temperature is in the range of from about room temperature to about 50° C. and the time may be from several hours at the lower temperature to about five minutes at the upper temperature. The product generally precipitates and may be purified by extraction in suitable organic solvents, subsequently washed and dried.

The amine or amino acid reactant employed preparing the conjugates of folic acid wherein $R^3$ is radical "A" have the following structural formula:

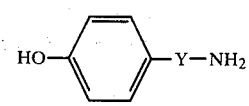 II wherein y is as defined above.

Examples of the compounds of Formula II that may be employed include: p-(aminomethyl)phenol, p-(β- aminoethyl)phenol(tyramine), p-(3-aminopropyl)-phenol, p-(2-aminopropyl)phenol, p-(8-aminooctyl)-phenol, p-(18-aminooctadecyl)phenol, tyrosine methyl ester, 4-hydroxyphenyl glycinate and the like.

The preferred reactant compounds are tyramine and the methyl ester of tyrosine. These compounds serve to introduce a phenolic group having both ortho positions (with respect to the hydroxy group) available and receptive to halogenation.

The resulting uniodinated conjugate of folic acid wherein both X's are hydrogen is readily iodinated to introduce one of the radioactive iodine isotopes ($^{125}I$ and $^{131}I$) into one or both of the ortho positions of the phenolic group. Iodination can be effected by mixing the uniodinated folic acid conjugate in an aqueous solution of sodium iodide in which the anion is one of the radioactive isotopes of iodine, such as mentioned above, and an oxidizing agent, such as (N-chloro-p-toluenesulfonamido) sodium, (Chloramine-T). The aqueous reaction medium is buffered at a pH of 6 to 8 and preferably above 7.4. After completion of the reaction, a reducing agent is added to neutralize any residual oxidizing agent and the iodinated folic acid conjugate is then separated from free radioactive iodine, for example, by electrophoresis or column chromatography.

The protein, "$R^3$", has a molecular weight in the range of from about 10,000 to 20,000,000 or more, which converts folic acid (normally a hapten) into a antigen that can be injected into the blood stream of a vertebrate, such as a rabbit, hamster, or sheep, to develop an antibody that is specific for folic acid and can be used in RIA procedures to assay body fluids for their content of folic acid.

Examples of proteins that can be covalently bonded with folic acid by reaction with the carboxylic group include blood proteins generally having molecular weights in the range of 3,000,000 to 20,000,000; and the globulins, albumins and fibrinogens having molecular weights in the range of 100,000 to 1,000,000. Specifically, bovine serum albumin, sheep serum albumin, rabbit serum albumin, goat serum albumin, human serum albumin, polylysine thyroglobulin and gamma-globulin may be used.

The same general procedure described above for making the folic acid conjugate wherein the X radicals are both hydrogen can be used for making the folic acid conjugate from the folic acid using the protein in place of the amine of Formula II.

Examples of the carbodiimides that may be made water soluble for use as a condensing agent include those of the formula: $R^5-N=C=N-R^5$ wherein $R^5$ is cycloalkyl having from 5 to 6 nuclear carbon atoms; alkyl of from 2 to 12 carbon atoms, e.g., ethyl, n-propyl, isopropyl, n-butyl, sec-butyl, isobutyl, tert-butyl, pentyl, hexyl, heptyl, octyl, nonyl, decyl, undecyl, dodecyl and the like; mononuclear aryl lower alkyl, for example, benzyl, $\alpha$- and $\beta$-phenylethyl; mononuclear aryl, for example, phenyl and the like; morpholinyl, piperidyl and the like; morpholinyl lower alkyl, for example, morpholinylethyl, piperidyl lower alkyl, for example, piperidylethyl, dialkyl aminoalkyl, for example, 3-diethylaminopropyl, 2-dimethylaminopropyl, 2-dimethylaminoethyl, 3-dimethylaminopropyl and the like; pyridyl lower alkyl, for example, pyridylmethyl, pyridylethyl and the like or an acid addition salt or quaternary ammonium salt thereof, with the proviso that at least one of the $R^5$ radicals is an amino nitrogen containing group.

The carbodiimides may be prepared in accordance with the general method of E. Schmidt, F. Hitzler and E. Lahde, Ber. 71, 1933 (1938) from the corresponding thioureas by oxidation with mercuric oxide in acetone. The thioureas may be prepared from the corresponding amines by reaction with carbon disulfide in the case of symmetrical thioureas. The unsymmetrical thioureas may be prepared in reaction of an amine with isothiocyanate. The carbodiimides are also preparable from the corresponding ureas.

The easily water soluble carbodiimides are most suitable for use in the present invention. If the carbodiimide has an amino group in one or both of the $R^5$ substituents, it may be made water soluble by forming an acid addition salt with a hydrohalic acid, for example, hydrochloric, hydrobromic or hydroiodic acid also sulfuric acid, sulfonic acids, nitric acid, phosphoric acid and phosphonic acid can be employed. Also, if the carbodiimide contains a tertiary amino group, it can be made water soluble by quaternization with a suitable quaternization agent, for example, methyl tosylate, methyl bromide, methyl iodide, benzyl bromide, ethyl iodide, ethyl bromide, benzyl iodide, ethyl tosylate, methyl sulfate, ethyl sulfate and the like.

Included within the scope of this invention are the salts of the instant products. In general, any base which will form a salt with the foregoing folic acid conjugates is considered as being within the scope of this invention; suitable bases include, for example, alkali metal and alkaline earth metal hydroxides, carbonates, bicarbonates and the like. Also included within the scope of this invention are the ester and amide derivatives of the instant products which are prepared by conventional methods wellknown to those skilled in the art. Esters which are preferred are lower alkyl esters containing from 1-6 carbon atoms such as the methyl, ethyl, propyl, butyl, pentyl and hexyl esters. Preferred amides are the mono- and di-lower alkyl amides. These esters and amides are considered as being functionally equivalent to the acids and salts of this invention.

The examples which follow illustrate the conjugates of folic acid (I) of this invention and the methods by which they are prepared; however, the examples are illustrative only and it will be apparent to those having ordinary skill in the art that all of the products embraced by Formula I (supra) may also be prepared in an analogous manner by substituting the appropriate starting materials for those set forth in the examples.

EXAMPLE 1—Folate Thyroglobulin Conjugate

Step A—Monosodium Salt of Folic Acid

Folic acid (1.0 g.) and, as a tracer, approximately 10,000,000 cpm of tritiated folic acid (a minute amount on the order of a milligram to a picogram) is suspended in water and saturated sodium bicarbonate is added until complete dissolution occurs. Acetone is then added to precipitate the salt. The solid monosodium salt of folic acid is collected by filtration, washed with acetone and dried to constant weight.

Step B—Folate Thyroglobulin Conjugate

Thyroglobulin (100 mg.) is dissolved in water (10 ml.). To this is added 1-ethyl-3-(3-dimethylaminopropyl) carbodiimide hydrochloride (50 mg.) followed by the addition of labeled sodium folate (40 mg.). After stirring at room temperature for two hours the mixture is dialyzed against running water for 24 hours and then against isotris buffer (a 1.0 M solution of tris-(hydroxymethyl)aminomethane-HCl) at a pH of 7.5, using a Cellophane membrane and then lyophilized to afford 140 mg. of folate thyroglobulin conjugate. An aliquot is counted for tritium and is calculated to contain 32 moles of folate per mole of thyroglobulin.

By following substantially the procedure of Example I, Step B, and by substituting the appropriate protein for thyroglobulin, folate conjugates are obtained from the following proteins: Methylated Bovine Serum Albumin (BSA); Sheep Serum Albumin (SSA); Rabbit Gamma Globulin (RGG), Porcine Serum Albumin (PSA), Polylysine and Human Serum Albumin (HSA).

EXAMPLE 2—Folic Acid-Tyrosine Methyl Ester Conjugate

Sodium folate (100 mg.) is dissolved in water (10 ml.). To this is added 1-ethyl-3-(3 dimethylaminopropyl)carbodiimide hydrochloride (100 mg.), followed by the addition of tyrosine methyl ester hydrochloride (32 mg.) dissolved in water (2 ml.). A yellow gelatinous precipitate forms. The mixture is stirred for four hours at room temperature. The precipitated material is extracted into ethyl acetate and washed successively with 1 N sodium bicarbonate ($3 \times 10$ ml.) 1 N hydrochloric acid ($3 \times 10$ ml.) and water ($2 \times 10$ ml.). The solution is dried over anhydrous magnesium sulfate and the ethyl acetate removed on a rotary evaporator. Trituration of the remaining residues with hexane yields yellow crystalline folic acid tyrosine methyl ester conjugate weighing 56 mg.

EXAMPLE 3—$^{125}$I Folic Acid-Tyrosine Methyl Ester (TME)

To folic acid-tyrosine methyl ester (2.5 $\mu$g.) is added 50 $\mu$l of 0.5 M phosphate buffer containing 1 mCi of Na $^{125}$I and then 30 $\mu$g Chloramine-T. The buffer solution to which the Na $^{125}$I is added contains 34 g. of $KH_2PO_4$ and 35.5 g. of anhydrous $Na_2HPO_4$ per liter of water. The reaction mixture is agitated for 30 seconds and then 60 $\mu$g of sodium metabisulfite is added. The iodinated conjugate is then separated from free $^{125}$I by column chromatography.

By following substantially the procedure of Example 3 replacing the folic acid-TMS conjugate with the corresponding tyramine, tyrosine ethyl ester, tyrosine n-butyl ester, p-(18 aminooctadecyl)phenol, tyrosine lauryl ester or tyrosine stearyl ester conjugates of folic acid there is obtained the corresponding radioactive $^{125}$I labeled products.

EXAMPLE 4—$^{131}$I-Folic Acid-Tyrosine Methyl Ester

By following substantially the procedure of Example 3 and by substituting Na $^{131}$I for the Na $^{125}$I employed therein there is obtained $^{131}$I folic acid tyrosine methyl ester.

The radioactive iodine isotope labeled folic acid conjugates show marked specific activity and sensitivity in assay, particularly when minute amounts of folic acid are to be assayed in human body fluids, such as blood serum or plasma. These iodine-labeled folic acid conjugates are reasonably stable and do not require liquid scintillation counting analysis of the samples.

The following example illustrates the manner of use of the conjugates of the present invention for the determination of folic acid by radioimmunoassay.

EXAMPLE 5—RIA Procedure

For RIA determination of folic acid, the following solutions and blood sera are used:

A. 0.01 M Phosphate buffer solution (PBS) which contains 0.68 g. $KH_2PO_4$ and 0.71 g. anhydrous $Na_2HPO_4$ in one liter of water herein referred to as Buffer A.

B. The same solution as in A except it also contains 1.46 g. (0.05 M) per liter of ethylenediaminetetraacetic acid herein referred to as Buffer B.

C. A first antibody serum against folic acid obtained from the blood of a rabbit that has been injected with the product of Example 1.

D. Normal rabbit serum obtained from a rabbit which has not been insulated with antigen to be assayed.

E. Normal rabbit serum diluted by mixing one part by volume of serum in D above with 100 parts by volume of Buffer B.

F. A solution of the first antibody in C above at a dilution of one part by volume per 1000 obtained by diluting one part of antibody solution C above to 100 parts with Buffer B solution and then diluting one ml. of the resulting diluted solution with nine ml. of the diluted solution obtained in E above.

G. A solution in Buffer A of $^{125}$I folic acid-TME has a gamma ray radioactivity of 30,000 to 50,000 counters per minute.

H. A second antibody serum obtained from the blood serum of a sheep injected with the gamma-globulin of a normal rabbit.

I. Human blood serum taken from a person whose folic acid level is to be determined.

J. 13.25 ml. of the second antibody serum H is added to one liter of Buffer A.

The RIA procedure consists of the following steps:

1. A mixture is made of 50 microliters of antibody solution F with 200 microliters of human blood serum I to be tested, 250 microliters of the EDTA-containing phosphate buffer solution B and 100 microliters of the $^{125}$I labeled solution G.

2. This mixture is incubated at room temperature for one to four hours.

3. Thereupon, 400 microliters of solution J is added.

4. The resulting solution is incubated for 24 to 48 hours at room temperature.

5. Thereafter, the product is centrifuged at 1000X for 30 minutes. The solid residue from the centrifuging is washed two times with 0.01 M phosphate buffer solution (Buffer A), centrifuging after each washing.

6. The resulting solid product is then subject to radioactivity detection as by means of a gamma-counter. The determination of the folic acid concentration in an unknown is done by comparison of bound counts with those obtained from various solutions of folic acid of known concentration.

What is claimed is:

1. A compound of the formula:

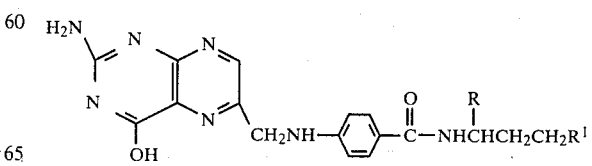

wherein R and $R^1$ are carboxy or a salt, ester or a mono- or dialkyl amide thereof or a radical of the formula:

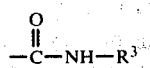
wherein -NH-R³ is a protein selected from thyroglobulin, methylated bovine serum albumin, sheep serum albumin, polylysine, or human serum albumin wherein one of the R and R¹ substituents is carboxy or a salt, ester or a mono- or di-alkyl amide thereof and the other R or R¹ substituent is said radical.